US010653730B2

United States Patent
Tanaka et al.

(10) Patent No.: US 10,653,730 B2
(45) Date of Patent: May 19, 2020

(54) LACTIC ACID BACTERIUM, DRUG, FOOD OR DRINK, AND FEED WHICH CONTAIN THE LACTIC ACID BACTERIUM

(71) Applicant: MORINAGA MILK INDUSTRY CO., LTD., Tokyo (JP)

(72) Inventors: Tomohiro Tanaka, Zama (JP); Noriyuki Iwabuchi, Zama (JP); Yohei Sato, Zama (JP); Kanetada Shimizu, Zama (JP); Toshitaka Odamaki, Zama (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/105,467

(22) Filed: Aug. 20, 2018

(65) Prior Publication Data

US 2018/0353557 A1    Dec. 13, 2018

Related U.S. Application Data

(62) Division of application No. 15/261,548, filed on Sep. 9, 2016, now Pat. No. 10,064,903, which is a division of application No. 14/759,124, filed as application No. PCT/JP2014/057319 on Mar. 18, 2014, now abandoned.

(30) Foreign Application Priority Data

Jul. 12, 2013 (JP) .................................. 2013-146319

(51) Int. Cl.
| | | |
|---|---|---|
| *A61K 39/02* | (2006.01) | |
| *A61K 35/747* | (2015.01) | |
| *C12R 1/225* | (2006.01) | |
| *A23L 33/135* | (2016.01) | |
| *A23K 10/12* | (2016.01) | |
| *A23K 10/16* | (2016.01) | |
| *A23K 10/18* | (2016.01) | |
| *A23L 2/52* | (2006.01) | |
| *A61K 35/74* | (2015.01) | |
| *A61K 39/145* | (2006.01) | |
| *A61K 35/00* | (2006.01) | |
| *A61K 39/00* | (2006.01) | |

(52) U.S. Cl.
CPC ............ *A61K 35/747* (2013.01); *A23K 10/12* (2016.05); *A23K 10/16* (2016.05); *A23K 10/18* (2016.05); *A23L 2/52* (2013.01); *A23L 33/135* (2016.08); *A61K 35/74* (2013.01); *A61K 39/145* (2013.01); *C12R 1/225* (2013.01); *A23V 2002/00* (2013.01); *A23Y 2220/63* (2013.01); *A61K 2035/11* (2013.01); *A61K 2039/523* (2013.01)

(58) Field of Classification Search
None
See application file for complete search history.

(56) References Cited

U.S. PATENT DOCUMENTS

| | | |
|---|---|---|
| 2004/0047849 A1 | 3/2004 | Hsu et al. |
| 2010/0143303 A1 | 6/2010 | Nishida et al. |
| 2010/0196341 A1 | 8/2010 | Wei et al. |
| 2011/0150852 A1 | 6/2011 | Chambaud et al. |
| 2011/0159552 A1 | 6/2011 | Masuda et al. |
| 2012/0208260 A1 | 8/2012 | Kim et al. |
| 2012/0220760 A1 | 8/2012 | Ushida et al. |

FOREIGN PATENT DOCUMENTS

| | | |
|---|---|---|
| CN | 101772571 A | 7/2010 |
| EP | 2 271 744 B1 | 3/2013 |
| EP | 2 990 045 A1 | 3/2016 |
| JP | 2006/288290 A | 10/2006 |
| JP | 2009-155221 A | 7/2009 |
| KR | 10-2004-0023755 A | 3/2004 |
| KR | 10-2011-0046020 A | 5/2011 |
| TW | 201121553 A1 | 7/2011 |
| WO | WO 2009/005124 A1 | 1/2009 |
| WO | WO 2011/027829 A1 | 3/2011 |
| WO | WO 2012/133827 A1 | 10/2012 |

OTHER PUBLICATIONS

Coeuret, V., et al., In vitro Screening of Potential Probiotic Activities of Selected Lactobacilli Isolated From Unpasteurized Milk Products for Incorporation Into Soft Cheese, Journal of Dairy Research 71:451-460, 2004.

Cukrowska, B., et al., Impact of Heat-Inactivated Lactobacillus casei and Lactobacillus paracasei Strains on Cytokine Responses in Whole Blood Cell Cultures of Children With Atopic Dermatitis, Folia Microbiology 55(3):277-280, 2010.

Delcenserie, V., et al., Immunomodulatory Effects of Probiotics in the Intestinal Tract, Current Issues in Molecular Biology 10:37-54, 2008.

Extended European Search Report received in corresponding European Patent Application No. 14823722.5, dated Oct. 14, 2016.

Hori, T., et al., Augmentation of Cellular Immunity and Reduction of Influenza Virus Titer in Aged Mice Fed Lactobacillus casei Strain Shirota, Clinical and Diagnostic Laboratory Immunology 9(1):105-108, Jan. 2002.

Ichikawa, S., et al., Orally Administered Lactobacillus paracasei KW3110 Induces in Vivo IL-12 Production, Bioscience, Biotechnology, and Biochemistry, vol. 73(7):1561-1565, 2009.

(Continued)

*Primary Examiner* — Jennifer E Graser

(74) *Attorney, Agent, or Firm* — Knobbe, Martens, Olson & Bear LLP

(57) ABSTRACT

A method for prophylaxis or treatment of a disease includes administering an an effective amount of an agent that contains cells of *Lactobacillus paracasei* MCC1849 (NITE BP-01633) to a subject in need of such prophylaxis or treatment. The disease can be one or more of an inflammatory disease, ulcer, food allergies, bronchial asthma, urticaria, pollinosis, anaphylactic shock or an opportunistic infection.

9 Claims, 2 Drawing Sheets

(56) References Cited

OTHER PUBLICATIONS

Inoue, R., et al., Nucleic Acids of Enterococcus faecalis strain EC-12 Are Potent Toll-Like Receptor 7 and 9 Ligands Inducing Interleukin-12 Production From Murine Splenocytes and Murine Macrophage Cell Line J774.1, FEMS Immunology and Medical Microbiology 61:94-102, 2011.

International Search Report received in International Patent Application No. PCT/JP2014/057319, dated Jun. 24, 2014.

Iwabuchi, N., et al., Anti-Infective Effects of Lactobacillus paracasei MoLac-1 That Strongly Induces Interleukin-12, Proceedings of the Annual Meeting of Japan Society for Bioscience, Biotechnology, and Agrochemistry, Mar. 23, 2012, p. 391.

Iwabuchi, N., et al. Immunomodulating and Anti-Infective Effects of a Novel Strain of Lactobacillus paracasei That Strongly Induces Interleukin-12, FEMS Immunology & Medical Microbiology 66:230-239, 2012.

Jahreis, G., et al., Influence of Probiotic Sausage (*Lactobacillus paracasei*) on Blood Lipids and Immunological Parameters of Healthy Volunteers, Food Research International 35:133-138, 2002.

Notice of Allowance received in corresponding Korean Patent Application No. 10-2015-7019036 dated Mar. 24, 2016.

Office Action received in corresponding Chinese Patent Application No. 201480010045.5 dated Sep. 5, 2016.

Ogawa, T., et al., Natural Killer Cell Activities of Synbiotic *Lactobacillus casei* ssp. *casei* in Conjunction with Dextran, Clinical and Experimental Immunology 143:103-109, 2005.

Peng, G.-C., and C.-H. Hsu, The Efficacy and Safety of Heat-Killed Lactobacillus paracasei for Treatment of Perennial Allergic Rhinitis Induced by House-Dust Mite, Pediatric Allergy Immunology 16:433-438, 2005.

Shida, K., et al., Induction of Interleukin-12 by Lactobacillus Strains Having a Rigid Cell Wall Resistant to Intracellular Digestion, Journal of Dairy Science 89:3306-3317, 2006.

Shida, K., et al., Peptidoglycan From Lactobacilli Inhibits Interleukin-12 Production by Macrophages Induced by Lactobacillus casei through Toll-Like Receptor 2-Dependent and Independent Mechanisms, Immunology 128:e858-e869, 2009.

Takeda, K., et al., Interleukin-12 Is Involved in the Enhancement of Human Natural Killer Cell Activity by Lactobacillus casei Shirota, Clinical and Experimental Immunology 146:109-115, 2006.

Tanaka, T., et al., The Effect of Heat Condition on Interleukin-12 Induction of Lactobacillus paracasei MoLac-1, Proceedings of the Annual Meeting of Japan Society for Bioscience, Biotechnology, and Agrochemistry, Mar. 23, 2012, p. 392.

Tsai, Y.-T., et al., Effect of the Administration of *Lactobacillus paracasei* subsp. *paracasei* NTU 101 on Peyer's Patch-Mediated Mucosal Immunity, International Immunopharmacology 10:791-798, 2010.

Tuo, T., et al., In vitro Assessment of Immunomodulating Activity of the Two Lactobacillus Strains Isolated From Traditional Fermented Milk, World Journal of Microbiology and Biotechnology 27:505-511, 2011.

Examination Report received in connection with Indian Patent Application No. 3938/CHENP/2015 dated Sep. 28, 2018.

LACTIC ACID BACTERIUM, DRUG, FOOD OR DRINK, AND FEED WHICH CONTAIN THE LACTIC ACID BACTERIUM

CROSS-REFERENCES TO RELATED APPLICATIONS

Any and all applications for which a foreign or domestic priority claim is identified in the Application Data Sheet as filed with the present application are hereby incorporated by reference under 37 CFR 1.57.

Technical Field

The present invention relates to a novel lactic acid bacterium belonging to *Lactobacillus paracasei*, a drug, food or drink, and feed which contain the lactic acid bacterium.

Background Art

It has been reported that some lactic acid bacteria show prophylactic action and defensive action against various infectious diseases (Non-patent document 1). It has also been reported that these actions of lactic acid bacteria are based on activation of cell-mediated host immunity, promotion of IgA secretion from mucosae, such as those of intestinal tract and respiratory organs (Non-patent document 1), and so forth. For example, it has been reported that lactic acid bacteria belonging to *Lactobacillus casei* induce production of cytokines such as IL-12 (interleukin-12) and IFN-γ (interferon-γ) by immunocompetent cells of hosts to activate cell-mediated host immunity and thereby defend the hosts from infection by influenza virus, and so forth (Non-patent documents 2 to 4).

IL-12 and IFN-γ are cytokines having an action of inducing differentiation of naive helper T cells into type 1 helper T cells (Th1), an action of activating natural killer cells (NK cells), and an action of promoting phagocytosis of cells such as macrophages, and are involved in defensive actions against infections by viruses or bacteria, and antitumor effect of hosts. Therefore, in order to acquire high prophylactic action and defensive action of lactic acid bacteria against infectious diseases, it is important to use a lactic acid bacterium having a potent IL-12 production-inducing ability. As such lactic acid bacteria, there is known the *Lactobacillus paracasei* FERM BP-11313 strain, which shows high survivability under acidic conditions, and superior IL-12 production-inducing ability (Patent document 1, in this reference, this strain is also referred to as MCC1375 strain).

There has also been suggested involvement of cell walls of lactic acid bacteria in the induction of IL-12 production by lactic acid bacteria (Patent document 2), and it has been reported that if lactic acid bacteria are treated with a cell wall-digesting enzyme (N-acetyl muramidase), the IL-12 production-inducing ability is spoiled (Non-patent document 5). It has been also suggested that RNAs contained in lactic acid bacteria participate in the induction of IL-12 production by lactic acid bacteria, and it has been reported that if dead cells of lactic acid bacteria killed by heating are treated with RNase, the IL-12 production-inducing ability is markedly spoiled (Non-patent document 6). There have so far been also provided immunostimulants utilizing RNA of lactic acid bacteria itself (Patent documents 3 and 4).

Since human bodies contain cell wall-digesting enzymes such as lysozyme having the N-acetyl muramidase activity against bacteria, it is considered that lactic acid bacteria taken into the bodies are influenced by those enzymes. Further, RNases exist everywhere in the environment, and they are extremely stable against heat. Therefore, they easily contaminate products, and they are not inactivated by sterilization or the like, and may remain in the products. Moreover, since RNases also exist in human bodies, for example, in saliva and digestive juices, it is considered that lactic acid bacteria are also influenced by RNases after they are orally taken into the bodies.

Even if lactic acid bacteria inherently have high IL-12-inducing ability, they may not maintain and exhibit sufficient IL-12-inducing ability in living bodies, because they are influenced by the cell wall-digesting enzymes (N-acetyl muramidase) and RNases existing in saliva or digestive juices. It is considered that secretion amounts of these cell wall-digesting enzymes and RNases differ among individuals, and it is strongly considered that such difference possibly provides differences of the effect observed among individuals.

PRIOR ART REFERENCES

Patent Documents

Patent document 1: International Patent Publication WO2012/133827
Patent document 2: Japanese Patent Laid-open (Kokai) No. 2009-155221
Patent document 3: International Patent Publication WO2009/005124
Patent document 4: International Patent Publication WO2011/027829

Non-Patent Documents

Non-patent document 1: Delcenserie, V. et al., Curr. Issues Mol. Biol. (2008) 10:37-54
Non-patent document 2: Hori T. et al., Clin. Diagn. Lab. Immunol. (2002) 9:105-108
Non-patent document 3: Takeda, K. et al., Clin. Exp. Immunol. (2006) 146:109-115
Non-patent document 4: Ogawa, T., Clin. Exp. Immunol. (2006) 143:103-109
Non-patent document 5: Shida, K. et al., J. Dairy Sci. (2006) 89:3306-3317
Non-patent document 6: Inoue, R. et al., FEMS Immnol. Med. Microbiol. (2011) 61:94-102

SUMMARY OF THE INVENTION

Object to be Achieved by the Invention

An object of the present invention is to provide a lactic acid bacterium useful for prophylaxis and defense against various infections, i.e., a lactic acid bacterium showing high IL-12 production-promoting action or immunostimulation action, which actions are preferably not easily reduced in human bodies etc.

Means for Achieving the Object

In order to achieve the aforementioned object, the inventors of the present invention assiduously searched for such target lactic acid bacteria, and found a novel strain of *Lactobacillus paracasei* having a high IL-12 production-promoting action. Thus, they accomplished the present invention.

That is, the present invention provides the *Lactobacillus paracasei* MCC1849 (NITE BP-01633) strain.

The present invention also provides a drug which contains the strain.

In a preferred embodiment of the aforementioned drug, the drug is for immunostimulation.

In a preferred embodiment of the aforementioned drug, the drug is for antivirus.

In a preferred embodiment of the aforementioned drug for antivirus, the drug is for anti-influenza virus.

The present invention also provides a food or drink which contains the strain.

The present invention also provides a feed which contains the strain.

The present invention also provides an IL-12 production-promoting agent which contains the strain.

In a preferred embodiment of the aforementioned IL-12 production-promoting agent, the agent is in the form of food or drink.

BRIEF DESCRIPTION OF THE DRAWINGS

FIG. 2A shows symptom scores determined after infection. The symbol * indicates presence of a statistically significant difference between the two groups on the observation day.

FIG. 2B shows virus concentrations in the lungs. The symbol * indicates presence of a statistically significant difference between the two groups. The statistical analysis was performed by using the Dunnett test.

DETAILED DESCRIPTION OF THE PREFERRED EMBODIMENT

Figure 1:
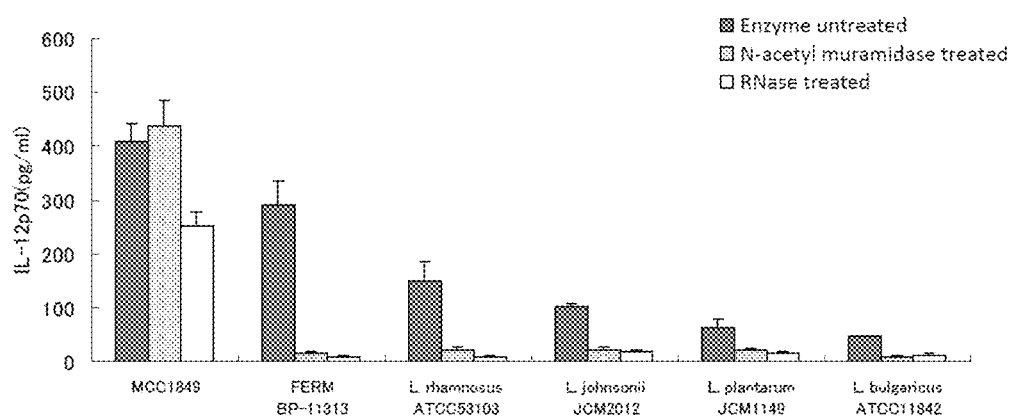
FIG. 1 shows amounts of IL-12 produced from mouse spleen cells in the presence of lactic acid bacteria. The lactic acid bacterium strains are indicated on the horizontal axis, and the vertical axis indicates average and standard deviation (S.D.) of the IL-12 production amount.

Hereafter, the present invention will be explained in detail.

The present invention relates to the *Lactobacillus paracasei* MCC1849 (NITE BP-01633) strain, which is a novel strain of a lactic acid bacterium belonging to *Lactobacillus paracasei*. This strain is henceforth also referred to as the "lactic acid bacterium of the present invention", or the "strain of the present invention", or simply as the MCC1849 strain.

The lactic acid bacterium of the present invention was isolated from human feces as an isolation source. The bacteriological characteristics of this strain will be shown in Example 1 described later. This strain was deposited on Jun. 6, 2013 at the independent administrative agency, National Institute of Technology and Evaluation, NITE Patent Microorganisms Depositary (#122, 2-5-8, Kazusakamatari, Kisarazu-shi, Chiba, 292-0818, Japan) with an accession number of NITE P-01633, and the deposit was converted to an international deposit under the provisions of the Budapest Treaty on Jan. 31, 2014, and given an accession number of NITE BP-01633.

DEPOSIT OF MICROORGANISM

*Lactobacillus paracasei* MCC1849 has been deposited on Jun. 6, 2013 at the independent administrative agency, National Institute of Technology and Evaluation, NITE Patent Microorganisms Depositary (#122, 2-5-8, Kazusakamatari, Kisarazu-shi, Chiba, 292-0818, Japan) with an accession number of NITE P-01633, and the deposit was converted to an international deposit under the provisions of the Budapest Treaty on the International Recognition of the Deposit of Microorganisms for the Purposes of Patent Procedure and the Regulations thereunder (Budapest Treaty) on Jan. 31, 2014, and given an accession number of NITE BP-01633. This assures maintenance of a viable culture of the deposit for 30 years from date of deposit. The deposit will be made available by NITE under the terms of the Budapest Treaty, and subject to an agreement between Applicant and NITE which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

The lactic acid bacterium of the present invention is not limited to the aforementioned deposited strain, and it may be a strain substantially equivalent to the deposited strain. Such a substantially equivalent strain is a strain belonging to *Lactobacillus paracasei*, exhibiting an IL-12 production-promoting action at a level comparable to that exhibited by the deposited strain, and preferably exhibiting reduction of the IL-12 production-promoting action at a low level comparable to that exhibited by the deposited strain even after a treatment with a cell wall-digesting enzyme or RNase. Moreover, the substantially equivalent strain further shows a homology of the nucleotide sequence of the 16S rRNA gene of 98% or more, preferably 99% or more, more preferably 100%, with respect to the nucleotide sequence of the 16S rRNA gene of the aforementioned deposited strain, and preferably has the same bacteriological characteristics as those of the aforementioned deposited strain. Furthermore, the lactic acid bacterium of the present invention may be a strain bred from the deposited strain or a strain substantially equivalent to the deposited strain by a mutation treatment, gene recombination, selection of a naturally mutated strain, or the like, so long as the effect of the present invention is not degraded.

The MCC1849 strain has a higher IL-12 (interleukin-12) production-promoting activity as compared with known lactic acid bacteria. Although the IL-12 production-promoting activity of lactic acid bacteria is generally markedly reduced by a treatment with a cell wall-digesting enzyme such as N-acetyl muramidase or RNase, the MCC1849 strain shows less reduction of the IL-12 production-promoting activity even after a treatment with a cell wall-digesting enzyme or RNase. The IL-12 production-promoting activity can be measured by the method described in the Example section.

The MCC1849 strain can be easily proliferated by, for example, culturing the strain. The culture method is not particularly limited so long as the MCC1849 strain can be proliferated, and a method usually used for culture of lactic acid bacteria can be appropriately modified as required, and used. For example, the culture temperature may be 25 to 50° C., and is preferably 35 to 42° C. Although the culture may be performed under aerobic conditions, or anaerobic conditions, the culture is preferably performed under anaerobic conditions, for example, with supplying an anaerobic gas such as carbon dioxide gas. The culture may also be performed under microaerobic conditions as liquid stationary culture, or the like.

The medium for culturing the MCC1849 strain is not particularly limited, and a medium usually used for culture of lactic acid bacteria can be appropriately modified as required, and used. That is, as a carbon source, for example, saccharides such as galactose, glucose, fructose, mannose, cellobiose, maltose, lactose, sucrose, trehalose, starch, starch hydrolysate, and blackstrap molasses can be used according to the assimilation characteristics. As a nitrogen source, for example, ammonia, ammonium salts such as ammonium sulfate, ammonium chloride, and ammonium nitrate, and nitrates can be used. Further, as inorganic salts, for example, sodium chloride, potassium chloride, potassium phosphate, magnesium sulfate, calcium chloride, calcium nitrate, manganese chloride, ferrous sulfate, and so forth can be used. Furthermore, organic components such as peptone, soybean flour, defatted soybean meal, meat extract, and yeast extract may also be used. Further, as a ready-made medium, for example, the MRS medium can be preferably used.

As the MCC1849 strain, culture obtained by culturing the strain may be used as it is, or may be used after dilution or concentration, or cells collected from the culture may also be used. Further, so long as the effect of the present invention is not degraded, various additional operations such as heating and lyophilization can be performed after the culture. Such additional operations are preferably those providing high live cell survivability. In the drug, food or drink, and feed of the present invention, the cells of the MCC1849 strain are preferably live cells, but they may be dead cells.

The MCC1849 strain can be used as an IL-12 production-promoting agent. The MCC1849 strain, an IL-12 production-promoting agent containing the strain, or a composition containing either one of them can be used for a wide rage of uses, for example, as a drug, food or drink, and feed. For example, a drug for promoting IL-12 production, a food or drink for promoting IL-12 production, and a feed for promoting IL-12 production can be provided.

Further, the IL-12 production-promoting agent of the present invention can be used as an immunostimulant or an antiviral agent. The virus as the target of the antiviral agent is not particularly limited so long as the disease caused by the virus can be prevented or treated by promotion of the IL-12 production or immunostimulation, and examples include, for example, influenza viruses.

The drug of the present invention is not particularly limited so long as the MCC1849 strain is contained. As the drug of the present invention, the MCC1849 strain per se may be used, or a pharmaceutical preparation thereof may be prepared by adding a physiologically acceptable liquid or solid carrier, and used.

The dosage form of the drug of the present invention is not particularly limited, and specific examples include tablet, pill, powder, solution, suspension, emulsion, granule, capsule, syrup, suppository, injection, ointment, patch, eye drop, nose drop, and so forth. Further, for preparation of a pharmaceutical preparation, there can be used additives such as excipient usually used as a carrier of pharmaceutical preparation, binder, disintegrating agent, lubricant, stabilizer, flavor, diluent, surfactant, and solvent for injection.

Although the content of the MCC1849 strain in the drug of the present invention is appropriately determined depending on the dosage form, direction for use, patient's age, sex, type of disease, severity of disease, and other conditions, it is usually preferably in the range of $1 \times 10^6$ to $1 \times 10^{12}$ cfu/g, or $1 \times 10^6$ to $1 \times 10^{12}$ cfu/ml, more preferably in the range of $1 \times 10^7$ to $1 \times 10^{11}$ cfu/g, or $1 \times 10^7$ to $1 \times 10^{11}$ cfu/ml. When the cells of the MCC1849 strain are dead cells, the unit of cfu/g or cfu/ml can be replaced with number of cells/g or number of cells/ml.

Further, so long as the effect of the present invention is not degraded, the drug containing the MCC1849 strain and another drug, for example, an IL-12 production-promoting agent, immunostimulant, antiviral agent, anti-inflammatory agent, antiulcer agent, or the like other than the MCC1849 strain can be used in combination.

The administration time of the drug of the present invention is not particularly limited, and it can be appropriately chosen according to the type of therapy for the objective disease. The drug of the present invention may be prophylactically administered, or used for maintenance therapy. The administration route is preferably determined according to the dosage form, patient's age, sex, other conditions, severity of symptoms of patient, and so forth. In any case, the drug of the present invention can be administered once or two or more times a day, or it may be administered once in several days or several weeks.

The IL-12 production-promoting agent of the present invention or a composition containing it comprises cells of the MCC1849 strain as an active ingredient, and can markedly promote production of IL-12 in a living body. The increased IL-12 activates the cell-mediated immunity. Therefore, the IL-12 production-promoting agent of the present invention can enhance the cell-mediated immunity, and thus it can be used also as an immunostimulant. The term "immunostimulation" means to stimulate various immunoreactions, and is synonymous with "immune activation". Further, the IL-12 production-promoting agent can also be used as an IL-12 production-inducing agent.

The drug or IL-12 production-promoting agent of the present invention has an IL-12 production-promoting action or an immunostimulation action based on the foregoing action, and can be used for a prophylactic or therapeutic treatment of a disease that can be prevented or cured by promotion of IL-12 production, or immunostimulation. The term "cure" also means to ameliorate a disease.

Specific examples of the application of the drug of the present invention include, for example, ameliorations of allergies such as food allergies, bronchial asthma, urticaria, rhinitis, pollinosis, and anaphylactic shock, as well as enhancement of resistance to infectious diseases, prophylaxis of cancer, prevention of advance of cancer, and so forth. Further, the drug or IL-12 production-promoting agent of the present invention can be widely used as an antitumor agent, a prophylactic or therapeutic agent for an opportunistic infection, or a prophylactic or therapeutic agent for an allergic disease.

The drug of the present invention may be independently administered, or may be used together with another drug such as an immunosuppressant.

Another aspect of the present invention is use of the MCC1849 strain in manufacture of an IL-12 production-promoting agent or an immunostimulant. A further aspect of the present invention is a method for prophylactic or therapeutic treatment of a disease which is preventable or curable by promotion of IL-12 production, which comprises the step of administrating the MCC1849 strain or the drug of the present invention to an object of application.

As another embodiment of the drug of the present invention, the drug of the present invention can be used as an antiviral agent, and in particular, it can be used as an anti-influenza virus agent. The anti-influenza virus agent of the present invention can be used for prophylactic or therapeutic treatment of a disease caused by an influenza virus. The anti-influenza virus agent of the present invention can reduce infection or proliferation of an influenza virus in a living body. The virus as an object of the antiviral agent is not particularly limited, so long as the disease caused by the virus can be prevented or cured by promotion of IL-12 production or immunostimulation.

Another aspect of the present invention is use of the MCC1849 strain in manufacture of an antiviral agent, for example, an anti-influenza virus agent. A further another aspect of the present invention is a method for prophylactic or therapeutic treatment of a disease caused by a virus, for example, influenza, which comprises the step of administrating the MCC1849 strain or the drug of the present invention to an object of application.

The food or drink of the present invention is not particularly limited so long as the MCC1849 strain is contained, and examples of the food or drink include drinks such as soft drinks, carbonated drinks, nutritious drinks, fruit-juice drinks, and lactic acid bacteria beverages (including concentrated undiluted solutions or powders for preparation of these drinks); frozen deserts such as ice cream, sherbet and chipped ice; confectioneries such as hard candy, chewing gum, candy, gum, chocolate, tablet confectioneries, snack, biscuit, jelly, jam, cream, and baked confectioneries; dairy products such as processed milk, milk beverages, fermented milk, drinkable yogurt, and butter; breads; foods for enteral feeding, liquid foods, infant formulas, sport drinks; other functional foods, and so forth. The food may be a supplement in the form of, for example, a tablet. When the food is a supplement, the MCC1849 strain can be taken without being influenced by other foods concerning daily amount of meals and ingested calories.

The food or drink of the present invention can be produced by adding the MCC1849 strain to a raw material of the food or drink, and can be produced in the same manner as those for usual foods or drinks except that the MCC1849 strain is added. The MCC1849 strain may be added at any stage of the manufacturing process of the food or drink. The food or drink may also be produced through a fermentation process advanced by the MCC1849 strain. Examples of such a food or drink include lactic acid bacteria beverages, fermented milks, and so forth.

As the raw material of the food or drink, raw materials used for producing usual drinks and foods can be used. The produced food or drink can be orally taken.

The food or drink of the present invention includes raw materials for food or drink production and those to be added to foods or drinks in the course of the food or drink production process or after the production, such as food additives. For example, the lactic acid bacterium of the present invention can be used as a starter for production of fermented milk. The lactic acid bacterium of the present invention can also be added to a produced fermented milk afterward.

Although the content of the MCC1849 strain in the food or drink of the present invention is appropriately determined according to the form of the food or drink, it is usually preferably in the range of $1\times10^6$ to $1\times10^{12}$ cfu/g, or $1\times10^6$ to $1\times10^{12}$ cfu/ml, more preferably in the range of $1\times10^7$ to $1\times10^{11}$ cfu/g, or $1\times10^7$ to $1\times10^{11}$ cfu/ml, of the food or drink.

The food or drink of the present invention can be used for various uses utilizing effects of IL-12 production promotion, immunostimulation, antivirus, and so forth. That is, there can be provided an IL-12 production-promoting agent, immunostimulant, and antiviral agent that contain the lactic acid bacterium of the present invention and are in the form of food or drink. The IL-12 production-promoting agent, immunostimulant, and antiviral agent in the form of a food or drink are synonymous with an IL-12 production-promoting agent containing the food or drink of the present invention, immunostimulant containing the food or drink of the present invention, and antiviral agent containing the food or drink of the present invention, respectively.

The food or drink of the present invention can be sold as a food or drink with indication of use, i.e., for promotion of IL-12 production, for immunostimulation, or for antivirus. Further, the food or drink of the present invention may have an indication such as "For promotion of IL-12 production", "For immunostimulation", "For immune activation", "For antivirus", "For anti-influenza virus", and "For prophylaxis of infectious disease". Further, indications other than those described above expressing an effect secondarily obtainable by promotion of IL-12 production can of course be used.

The aforementioned term "indication" includes all actions for informing consumers of the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use.

Specific examples include actions of indicating the aforementioned use on goods or packages of goods relating to the food or drink of the present invention, actions of assigning, delivering, displaying for the purpose of assigning or delivering, or importing such goods or packages of goods on which the aforementioned use is indicated, displaying or distributing advertisements, price lists or business papers relating the goods on which the aforementioned use is indicated, or providing information including those as contents with indicating the aforementioned use by an electromagnetic method (Internet etc.) and so forth. Indications on packages, containers, catalogues, pamphlets, advertisement materials used at the sales spots such as POPs, and other papers are especially preferred.

The indication is preferably an indication approved by the administration etc. (for example, an indication in a form based on an approval, which is qualified on the basis of any of various legal systems provided by the administration). Examples of the indication further include, for example, indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more specifically, typical examples include indications as food for specified health uses (especially indications of use for health) provided in the enforcement regulations of Health Promotion Law (Japanese Ministry of Health, Labor and Welfare, Ministerial ordinance No. 86, Apr. 30, 2003) and similar indications.

Examples of the feed of the present invention include pet foods, feeds for farm animals, feeds for fish culture, and so forth. The feed of the present invention can be produced by mixing the MCC1849 strain with a common feed material, for example, cereals, lees, bran, fish meal, bone meal, oil and fat, skim milk powder, whey, mineral feed, and yeast. Further, the feed may be produced through a fermentation process advanced by the MCC1849 strain as in the case of, for example, silage. The produced feed can be orally given to common mammals, livestock, bred fish, pets, and so forth.

Although the content of the MCC1849 strain in the feed of the present invention is appropriately determined according to the form of the feed, and object to which the feed is given, it is usually preferably in the range of $1 \times 10^6$ to $1 \times 10^{12}$ cfu/g, or $1 \times 10^6$ to $1 \times 10^{12}$ cfu/ml, more preferably in the range of $1 \times 10^7$ to $1 \times 10^{11}$ cfu/g, or $1 \times 10^7$ to $1 \times 10^{11}$ cfu/ml.

EXAMPLES

Hereafter, the present invention will be further specifically explained with reference to examples. However, the present invention is not limited by the following examples.

Example 1

Bacteriological Characteristics of the MCC1849 Strain

The MCC1849 strain was isolated from a human feces sample. As the bacteriological characteristics of the strain, those concerning cell morphology, mobility, sporulation, Gram staining, catalase, gas production from glucose, and sugar fermentability are shown in Table 1. The sugar fermentability was investigated by using a bacterium identification kit, API 50CH (Sysmex Biomerieux Co., Ltd.). That is, according to the method described in the manual attached to the kit, the bacterium was cultured overnight, the bacterium suspension was inoculated on a medium containing an objective substrate, the bacterium was cultured in an incubator at 37° C., and fermentation state of the substrate was evaluated on days 1 and 2 of the culture.

The bacteriological characteristics are shown in Table 1. On the basis of these results, the MCC1849 strain was determined to be *Lactobacillus paracasei*.

TABLE 1

Bacteriological characteristics of *Lactobacillus paracasei* MCC1849 strain

| | | |
|---|---|---|
| 1 | Cell morphology | Rod |
| 2 | Mobility | None |
| 3 | Sporulation | None |
| 4 | Gram staining | + |
| 5 | Catalase | − |
| 6 | Gas production from glucose | − |
| 7 | Sugar fermentability | |
| | (1) Control | − |
| | (2) Glycerol | − |
| | (3) Erythritol | − |
| | (4) D-Arabinose | − |
| | (5) L-Arabinose | − |
| | (6) D-Ribose | + |
| | (7) D-Xylose | − |
| | (8) L-Xylose | − |
| | (9) D-Adonitol | − |
| | (10) Metyl-β-D-Xylopyranoside | − |
| | (11) D-Galactose | + |
| | (12) D-Glucose | + |
| | (13) D-Fructose | + |
| | (14) D-Mannose | + |

TABLE 1-continued

Bacteriological characteristics of *Lactobacillus paracasei* MCC1849 strain

| | | |
|---|---|---|
| | (15) L-Sorbose | − |
| | (16) L-Rhamnose | − |
| | (17) Dulcitol | − |
| | (18) Inositol | − |
| | (19) D-Mannitol | + |
| | (20) D-Sorbitol | + |
| | (21) Metyl-α-D-Mannopyranoside | − |
| | (22) Metyl-α-D-glucopyranoside | ± |
| | (23) N-acetylglucosamine | ± |
| | (24) Amygdalin | ± |
| | (25) Arbutin | + |
| | (26) Esculine ferric citrate | + |
| | (27) Salicin | + |
| | (28) D-Cellobiose | + |
| | (29) D-Maltose | + |
| | (30) D-Lactose | + |
| | (31) D-Melibiose | − |
| | (32) D-Sucrose | + |
| | (33) D-Trehalose | + |
| | (34) Inulin | + |
| | (35) D-Melezitose | + |
| | (36) D-Raffinose | − |
| | (37) Starch | − |
| | (38) Glycogen | − |
| | (39) Xylitol | − |
| | (40) Gentiobiose | ± |
| | (41) D-Turanose | + |
| | (42) D-Lyxose | − |
| | (43) D-Tagatose | + |
| | (44) D-Fucose | − |
| | (45) L-Fucose | − |
| | (46) D-Arabitol | − |
| | (47) L-Arabitol | − |
| | (48) Gluconate | ± |
| | (49) 2-Ketogluconate | − |
| | (50) 5-Ketogluconate | − |

+: Positive;
−: Negative;
±: False positive

Further, on the basis of the analysis of 16S rRNA gene nucleotide sequence of the MCC1849 strain, the MCC1849 strain was determined to be *Lactobacillus paracasei* or *Lactobacillus casei*. *Lactobacillus paracasei* and *Lactobacillus casei* are closely related species, and it has been demonstrated that the homology of the 16S rRNA gene nucleotide sequences of the standard strains of them is 99% or higher (Huang C. H., and Lee F. L., Antonie Van Leeuwenhoek, 2011, 99(2):319-27). The genome sequence of the MCC1849 strain was determined, and the homology was confirmed by mapping the read using the genome of the *Lactobacillus paracasei* standard strain (ATCC 25302), or the *Lactobacillus casei* standard strain (ATCC 393) as the reference genome.

As a result, the MCC1849 strain showed a homology of 85% with respect to the *Lactobacillus paracasei* standard strain, whereas it showed a homology of 45% with respect to the *Lactobacillus casei* standard strain.

Therefore, it was confirmed that the MCC1849 strain is *Lactobacillus paracasei*.

Example 2

Evaluation of IL-12 Production-inducing Ability Using Mouse Spleen Cells

The effect of an RNase treatment or cell wall-digesting enzyme treatment on the IL-12 production-inducing ability of lactic acid bacteria was evaluated by using mouse spleen cells, for the *Lactobacillus paracasei* MCC1849 strain described in Example 1, and the *Lactobacillus paracasei* FERM BP-11313 strain (International Patent Publication WO2012/133827), which is known to have high IL-12 production-inducing ability, as well as other lactic acid bacterium strains, the *Lactobacillus rhamnosus* ATCC 53103 strain, *Lactbacillus johnsonii* JCM 2012 strain, *Lactobacillus plantarum* JCM 1149 strain, and *Lactobacillus bulgaricus* ATCC 11842 strain.

The FERM BP-11313 strain was deposited as an international deposit at the National Institute of Technology and Evaluation, NITE Patent Microorganisms Depositary. The JCM 2012 strain and the JCM 1149 strain are available from the independent administrative agency, Institute of Physical and Chemical Research, Japan Collection of Microorganisms (JCM) (2-1, Hirosawa, Wako-shi, Saitama-ken, 351-0198). Further, the ATCC 53103 strain and the ATCC 11842 strain are available from the American Type Culture Collection (address, 12301 Parklawn Drive, Rockville, Md. 20852, United States of America).

Each of the aforementioned lactic acid bacterial strains was cultured in the MRS (de Man Rogasa Sharpe) medium (BD Company) for 16 hours, and the cells were washed 3 times by centrifugation and re-suspension in distilled water, then suspended in distilled water at a density of 10 mg (in terms of dry weight of cells)/ml, and subjected to a heat treatment at 100° C. for 15 minutes to obtain a lactic acid bacterium dead cell suspension ("enzyme untreated").

Each lactic acid bacterium dead cell suspension was centrifuged, the supernatant was removed, the precipitates were suspended in a 50 mM Tris-malate buffer (pH 7.0) containing 4 mM magnesium chloride at a concentration of 10 mg (in terms of dry weight of cells)/ml, N-acetyl muramidase (N-Acetylmuramidase SG, Seikagaku Corporation) was added to the suspension at a concentration of 5 µg/ml, and the reaction was allowed at 37° C. for 120 minutes. Then, the enzyme was inactivated by a heat treatment at 100° C. for 5 minutes to obtain a cell wall-digesting enzyme-treated product ("N-acetyl muramidase treated").

Further, 0.1 mg/ml of ribonuclease A (RNase A, Life Technologies) was added to each lactic acid bacterium dead cell suspension, and an enzyme treatment was performed at 37° C. for 30 minutes. After the treatment, the precipitates were washed 3 times by centrifugation and re-suspension in distilled water, and then suspended again in distilled water at a concentration of 10 mg (in terms of dry weight of cells)/ml to obtain an RNase-treated product ("RNase treated").

As the experimental animals, 7-week old male BALB/c mice (Japan SLC) were used, and dissected at 7 to 9 weeks old to extract spleens. Spleen cells were collected from the extracted spleens, treated with an erythrocyte lysis solution (0.144 M ammonium chloride, 17 mM trishydroxymethyl-aminomethane, pH 7.65) for 2 minutes, and centrifuged to obtain spleen cells free from the erythrocyte fraction. To these spleen cells, and each of the lactic acid bacterium dead cell suspension (enzyme untreated), the cell wall-digesting enzyme treated product (N-acetyl muramidase treated), and the RNase treated product (RNase treated), which were prepared above, a medium obtained by adding 10% FBS (fetal bovine serum, Life Technologies), 100 IU/ml penicillin, and 0.1 mg/ml streptomycin to RPMI1640 (SIGMA-ALDRICH) was added to prepare test solutions containing $2.5 \times 10^6$ spleen cells/ml and 5 µg (in terms of dry weight of cells)/ml as the final concentration of the lactic acid bacterium dead cell suspension, the cell wall-digesting enzyme treated product, or the RNase treated product. Each test solution was applied in a volume of 200 µl to a 96-well microplate (BD Company), and incubation was performed at 37° C. in the presence of 5% $CO_2$.

After 2 days, the culture supernatant was collected, and the concentration of IL-12 p70 (p40-p35 heterodimer) in the culture supernatant was measured by using a measurement kit (Mouse IL-12 p70 DuoSet, R&D Systems).

The test was performed in triplicate, and the results are shown in Table 2 and FIG. 1.

TABLE 2

Amount of IL-12 prodced by mouse spleen cells with lactic acid bacteria

| | IL-12 production amount (pg/ml) (Average ± S.D.) | | |
|---|---|---|---|
| Strain | Enzyme untreated | N-Acetyl muramidase treated | RNase treated |
| MCC1849 | 407.6 ± 35.3 | 436.7 ± 49.1 | 252.8 ± 25.0 |
| FERM BP-11313 | 291.8 ± 42.6 | 15.7 ± 1.5 | 9.1 ± 1.8 |
| ATCC 53103 | 148.5 ± 38.7 | 22.1 ± 2.9 | 8.5 ± 3.2 |
| JCM 2012 | 101.3 ± 6.7 | 19.7 ± 6.8 | 17.5 ± 2.4 |
| JCM 1149 | 63.3 ± 15.2 | 20.7 ± 2.2 | 14.5 ± 3.4 |
| ATCC 11842 | 47.1 ± 1.0 | 8.7 ± 2.8 | 11.6 ± 5.2 |

The *Lactobacillus paracasei* MCC1849 strain showed an IL-12 production-inducing ability higher than that of the FERM BP-11313 strain, which is known to have high IL-12 production-inducing ability. The IL-12 production-inducing abilities of the other lactic acid bacterium strains were lower than those of the aforementioned strains.

By the N-acetyl muramidase treatment or RNase treatment, the IL-12 production-inducing abilities of the lactic acid bacterium strains other than the MCC1849 strain were markedly reduced. However, the MCC1849 strain maintained the high IL-12 production-inducing ability even after it was subjected to the aforementioned treatments. Since the IL-12 production-inducing activity of the FERM BP-11313 strain, which is a strain of the same species as the MCC1849 strain, was degraded by the N-acetyl muramidase treatment or RNase treatment, it was demonstrated that the stability of the IL-12 production-inducing ability of the MCC1849 strain is not species-dependent property, but a strain-specific property.

Example 3

Influenza Virus Infection-Preventing Action of MCC1849 Strain

The influenza virus infection-preventing action by administration of the MCC1849 strain was investigated by using mice.

The MCC1849 strain was cultured in the MRS medium for 16 hours, the cells were washed twice with distilled water, and then suspended in distilled water, sucrose and sodium glutamate were added to the suspension, and the mixture was lyophilized. The lyophilized cells were suspended in physiological saline at a density of $1 \times 10^{10}$ cfu/ml to prepare an MCC1849 strain live cell suspension.

The MCC1849 strain was cultured in the MRS medium for 16 hours, the cells were washed twice with PBS, and once with distilled water, then suspended in distilled water, and subjected to a heat treatment at 100° C. for 30 minutes. After the heat treatment, the cells were washed twice with distilled water, suspended in distilled water, and lyophilized.

The lyophilized cells were suspended in physiological saline at a concentration of 5 mg/ml to prepare an MCC1849 strain dead cell suspension.

Each of the live cell suspension (Live group) of the MCC1849 strain, the dead cell suspension (HK group) of the same, and physiological saline (Control group) was orally administered in a volume of 0.2 ml to BALB/c mice for 14 days, and then the mice were infected with an influenza virus (A/PR8/34(H1N1) strain) from the nasal cavity. Six days after the infection, general statuses of the eyes (degree of opening of eyelid and state of eyelid), hair (lie of hair and piloerection), respiration (irregular respiration), and behavior (degree of spontaneous behavior) of the mice were observed, and the results of those items were represented with scores according to the following criteria to evaluate the onset state of the disease.

Normal state: 0
Slight infection: 1
Moderate infection: 2
Severe infection: 3
Death: 4

The average of the scores for the items was used as a symptom score for each mouse individual.

Further, 6 days after the infection, the lungs were extracted, and the virus concentrations in the lungs were measured by the plaque assay method using the MDCK cells (canine-derived kidney cells).

Figure 2A:
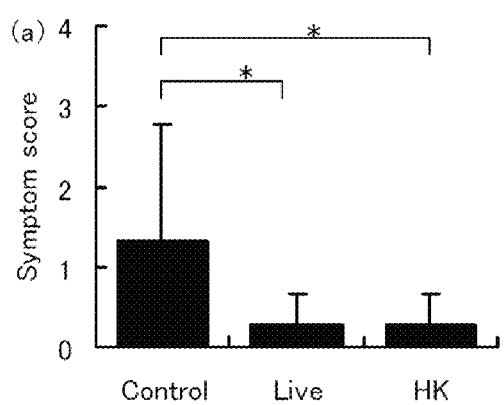
FIGS. 2A and 2B show influenza virus infection-preventing action of the MCC1849 strain.
Figure 2B:
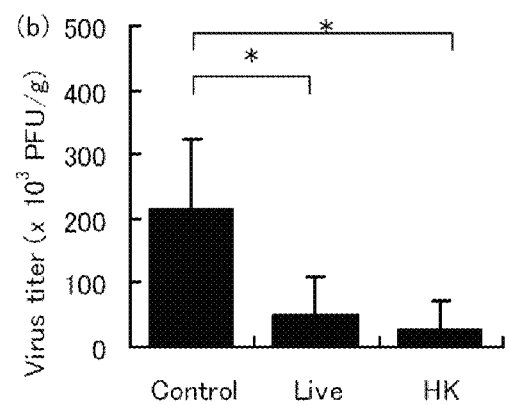

The test results are shown in Table 3 and FIG. 2.

Compared with the MCC1849 strain non-administration group (Control group), the symptom score was significantly reduced, and the virus concentration in the lungs (virus titer) was also significantly reduced by administration of either one of the MCC1849 strain live cell suspension (Live group) and the MCC1849 strain dead cell suspension (HK group). On the basis of these results, it was demonstrated that administration of the MCC1849 strain both in the live cell state and the dead cell state is effective for the prophylaxis of influenza virus infection.

TABLE 3

Influenza virus infection-preventing action of MCC1849

|  | Symptom score (Average ± S.D.) | Virus concentration in lung ($\times 10^3$ PFU) (Average ± S.D.) |
| --- | --- | --- |
| Pysiological saline (Control group) | 1.31 ± 1.47 | 215.6 ± 109.4 |
| Live cell suspension (Live group) | 0.26 ± 0.41 | 47.7 ± 62.6 |
| Dead cell suspension (HK group) | 0.26 ± 0.41 | 24.8 ± 44.9 |

INDUSTRIAL APPLICABILITY

The strain of the present invention, the *Lactobacillus paracasei* MCC1849 strain, has high IL-12 production-promoting activity. The IL-12 production-promoting activity of the strain is hardly reduced by a cell wall-digesting enzyme treatment or an RNase treatment. Therefore, it is thought that individual differences of the IL-12 production-promoting activity observed among objects of the application thereof would be small, and thus the strain is useful as an immunostimulant. Further, the strain can reduce infection or proliferation of influenza virus etc., and can be used for prophylactic and therapeutic treatments of infectious diseases, and so forth.

What is claimed is:

1. A method for prophylaxis of a disease, comprising administering an agent that comprises cells of *Lactobacillus paracasei* MCC1849 (NITE BP-01633) to a subject in need thereof in an effective amount,
   wherein the disease is one or more selected from the group consisting of inflammatory, ulcer, food allergies, bronchial asthma, urticaria, pollinosis, anaphylactic shock and an opportunistic infection.

2. The method according to claim 1, wherein the agent is a drug, food, drink or feed.

3. A method for treating a disease, comprising administering a drug which comprises cells of *Lactobacillus paracasei* MCC1849 (NITE BP-01633) to a subject in need thereof in an effective amount,
   wherein the disease is one or more selected from the group consisting of inflammatory, ulcer, food allergies, bronchial asthma, urticaria, pollinosis, anaphylactic shock and an opportunistic infection.

4. The method according to claim 3, wherein the cells are live cells.

5. The method according to claim 3, wherein the cells are heat-treated cells and/or enzyme-treated cells.

6. The method according to claim 5, wherein the heat-treated cells and/or the enzyme-treated cells are dead cells.

7. The method according to claim 4, wherein the cells are administered at a dose of $10^6$ to $10^{12}$ cfu/g or $10^6$ to $10^{12}$ cfu/ml.

8. The method according to claim 5, wherein the cells are administered at a dose of $10^6$ to $10^{12}$ cells/g or $10^6$ to $10^{12}$ cells/ml.

9. The method according to claim 8, wherein the heat-treated cells and/or the enzyme-treated cells are dead cells.

* * * * *

UNITED STATES PATENT AND TRADEMARK OFFICE
CERTIFICATE OF CORRECTION

PATENT NO. : 10,653,730 B2
APPLICATION NO. : 16/105467
DATED : May 19, 2020
INVENTOR(S) : Tomohiro Tanaka Page 1 of 1

It is certified that error appears in the above-identified patent and that said Letters Patent is hereby corrected as shown below:

On the Title Page

In Column 2, item (57), Abstract, Line 2, delete "an an" and insert -- an --.

In the Specification

In Column 1, Line 34, delete "4) ." and insert -- 4). --.

In Column 5, Line 39, delete "rage" and insert -- range --.

In Column 7, Line 28, delete "deserts" and insert -- desserts --.

In Column 8, Line 54, delete "Labor" and insert -- Labour --.

In Column 8, Line 65, delete "Labor" and insert -- Labour --.

In Column 10, Line 62, delete "inducing" and insert -- Inducing --.

In Column 11, Line 6, delete "Lactbacillus" and insert -- Lactobacillus --.

In Column 11, Line 21, delete "Rogasa" and insert -- Rogosa --.

In Column 12, Line 13 (approx.), delete "prodced" and insert -- produced --.

In Column 13, Line 9, delete "(A/PR8/34(H1N1)" and insert -- (A/PR/8/34 (H1N1) --.

In Column 13, Line 46, delete "Pysiological" and insert -- Physiological --.

Signed and Sealed this
Tenth Day of November, 2020

Andrei Iancu
*Director of the United States Patent and Trademark Office*